US008229126B2

(12) United States Patent
Chamberlain et al.

(10) Patent No.: US 8,229,126 B2
(45) Date of Patent: Jul. 24, 2012

(54) NOISE ERROR AMPLITUDE REDUCTION

(75) Inventors: Mark Chamberlain, Honeoye Falls, NY (US); Anthony Richard Alan Keane, Webster, NY (US)

(73) Assignee: Harris Corporation, Melbourne, FL (US)

( * ) Notice: Subject to any disclaimer, the term of this patent is extended or adjusted under 35 U.S.C. 154(b) by 707 days.

(21) Appl. No.: 12/403,646

(22) Filed: Mar. 13, 2009

(65) Prior Publication Data

US 2010/0232616 A1 Sep. 16, 2010

(51) Int. Cl.
*A61F 11/06* (2006.01)

(52) U.S. Cl. ...... 381/71.1; 381/57; 381/71.7; 381/71.11

(58) Field of Classification Search .................... 381/57, 381/71.1, 71.7, 71.11
See application file for complete search history.

(56) References Cited

U.S. PATENT DOCUMENTS 3,728,633 A 4/1973 Krebs
4,225,976 A 9/1980 Osborne et al.
4,672,674 A * 6/1987 Clough et al. ............... 381/94.7
4,831,624 A 5/1989 McLaughlin et al.
5,224,170 A 6/1993 Waite, Jr.
5,226,178 A 7/1993 Eastmond et al.
5,260,711 A 11/1993 Sterzer
5,303,307 A * 4/1994 Elko et al. ....................... 381/92
5,377,275 A 12/1994 Suzuki et al.
5,381,473 A 1/1995 Andrea et al.
5,473,684 A * 12/1995 Bartlett et al. ................ 379/395
5,473,702 A 12/1995 Yoshida et al.
5,673,325 A * 9/1997 Andrea et al. .................. 381/92
5,732,143 A 3/1998 Andrea et al.
5,754,665 A 5/1998 Hosoi et al.
5,838,269 A 11/1998 Xie
5,917,921 A 6/1999 Sasaki et al.
5,969,838 A * 10/1999 Paritsky et al. ............... 398/136
6,032,171 A 2/2000 Kiriaki et al.
6,061,456 A 5/2000 Andrea et al.
6,246,773 B1 6/2001 Eastty et al.
6,501,739 B1 12/2002 Cohen et al.
6,549,586 B2 4/2003 Gustafsson et al.
6,564,184 B1 5/2003 Eriksson et al.
6,577,966 B2 * 6/2003 Balan et al. ..................... 702/76
6,654,468 B1 11/2003 Thompson
6,674,865 B1 1/2004 Venkatesh et al.
6,766,190 B2 7/2004 Ferek-Petric et al.
6,868,365 B2 * 3/2005 Balan et al. ................... 702/180
6,912,387 B2 6/2005 Haas et al.

(Continued)

OTHER PUBLICATIONS

Widrow, et al., "Adaptive Noice Cancelling: Principles and Applications". Proceedings of the IEEE, vol. 63, No. 12, Dec. 1975, pp. 1692-1716.

(Continued)

*Primary Examiner* — David S. Warren
(74) *Attorney, Agent, or Firm* — Fox Rothschild, LLP; Robert J. Sacco

(57) ABSTRACT

Systems (200) and methods (100) for noise error amplitude reduction. The methods involve configuring a first microphone system (202) and a second microphone system (302) so that far field sound originating in a far field environment relative to the first and second microphone systems produces a difference in sound signal amplitude at the first and second microphone systems. The difference has a known range of values. The methods involve (128) dynamically identifying the far field sound based on the difference. The methods also involve (130, 132, 134) automatically reducing substantially to zero a gain applied to the far field sound responsive to the identifying step.

21 Claims, 8 Drawing Sheets

U.S. PATENT DOCUMENTS

| | | | |
|---|---|---|---|
| 6,917,688 | B2 | 7/2005 | Yu et al. |
| 6,963,649 | B2 | 11/2005 | Vaudrey et al. |
| 6,978,010 | B1 | 12/2005 | Short et al. |
| 7,065,206 | B2 | 6/2006 | Pan |
| 7,092,529 | B2 | 8/2006 | Yu et al. |
| 7,146,013 | B1 | 12/2006 | Saito et al. |
| 7,191,127 | B2 | 3/2007 | Lorenzo et al. |
| 7,206,418 | B2 * | 4/2007 | Yang et al. .......... 381/92 |
| 7,248,708 | B2 * | 7/2007 | Vaudrey et al. .......... 381/94.7 |
| 7,274,794 | B1 * | 9/2007 | Rasmussen .......... 381/92 |
| 7,346,176 | B1 * | 3/2008 | Bernardi et al. .......... 381/92 |
| 7,359,504 | B1 | 4/2008 | Reuss et al. |
| 7,415,294 | B1 * | 8/2008 | Zhang et al. .......... 455/575.6 |
| 7,433,463 | B2 | 10/2008 | Alves et al. |
| 7,464,029 | B2 | 12/2008 | Visser et al. |
| 7,477,751 | B2 * | 1/2009 | Lyon et al. .......... 381/96 |
| 7,561,700 | B1 * | 7/2009 | Bernardi et al. .......... 381/92 |
| 7,688,985 | B2 | 3/2010 | Roeck |
| 7,697,700 | B2 * | 4/2010 | Mao .......... 381/94.3 |
| 7,751,575 | B1 * | 7/2010 | Baumhauer et al. .......... 381/92 |
| 7,826,623 | B2 * | 11/2010 | Christoph .......... 381/92 |
| 7,864,969 | B1 * | 1/2011 | Ma et al. .......... 381/92 |
| 7,876,918 | B2 * | 1/2011 | Luo .......... 381/317 |
| 7,961,869 | B1 * | 6/2011 | Zhang et al. .......... 379/420.04 |
| 7,983,720 | B2 * | 7/2011 | Chen .......... 455/575.1 |
| 7,983,907 | B2 * | 7/2011 | Visser et al. .......... 704/227 |
| 2002/0048377 | A1 * | 4/2002 | Vaudrey et al. .......... 381/94.7 |
| 2002/0116187 | A1 * | 8/2002 | Erten .......... 704/233 |
| 2002/0193130 | A1 * | 12/2002 | Yang et al. .......... 455/501 |
| 2003/0228023 | A1 | 12/2003 | Burnett et al. |
| 2005/0031136 | A1 * | 2/2005 | Du et al. .......... 381/92 |
| 2005/0075870 | A1 | 4/2005 | Chamberlain |
| 2005/0136848 | A1 | 6/2005 | Murray |
| 2006/0002570 | A1 * | 1/2006 | Vaudrey et al. .......... 381/92 |
| 2006/0013412 | A1 * | 1/2006 | Goldin .......... 381/94.1 |
| 2006/0120537 | A1 | 6/2006 | Burnett et al. |
| 2006/0133621 | A1 | 6/2006 | Chen et al. |
| 2006/0133622 | A1 | 6/2006 | Chen |
| 2006/0135085 | A1 | 6/2006 | Chen |
| 2006/0154623 | A1 * | 7/2006 | Chen et al. .......... 455/116 |
| 2006/0210058 | A1 * | 9/2006 | Kock et al. .......... 379/430 |
| 2007/0086603 | A1 * | 4/2007 | Lyon et al. .......... 381/96 |
| 2007/0116300 | A1 * | 5/2007 | Chen .......... 381/92 |
| 2007/0127736 | A1 * | 6/2007 | Christoph .......... 381/92 |
| 2007/0127759 | A1 | 6/2007 | Zhang et al. |
| 2007/0189561 | A1 | 8/2007 | Dijkstra et al. |
| 2007/0189564 | A1 | 8/2007 | McBagonluri et al. |
| 2007/0274552 | A1 | 11/2007 | Konchitsky et al. |
| 2008/0013770 | A1 | 1/2008 | Wu et al. |
| 2008/0019548 | A1 * | 1/2008 | Avendano .......... 381/313 |
| 2008/0044036 | A1 | 2/2008 | Konchitsky |
| 2008/0112570 | A1 | 5/2008 | Asada et al. |
| 2008/0175408 | A1 * | 7/2008 | Mukund et al. .......... 381/94.1 |
| 2008/0201138 | A1 * | 8/2008 | Visser et al. .......... 704/227 |
| 2008/0260175 | A1 * | 10/2008 | Elko .......... 381/73.1 |
| 2008/0269926 | A1 | 10/2008 | Xiang et al. |
| 2009/0003640 | A1 * | 1/2009 | Burnett .......... 381/355 |
| 2009/0010449 | A1 * | 1/2009 | Burnett .......... 381/92 |
| 2009/0010450 | A1 * | 1/2009 | Burnett .......... 381/92 |
| 2009/0010451 | A1 * | 1/2009 | Burnett .......... 381/92 |
| 2009/0010453 | A1 * | 1/2009 | Zurek et al. .......... 381/94.5 |
| 2009/0089053 | A1 * | 4/2009 | Wang et al. .......... 704/233 |
| 2009/0089054 | A1 * | 4/2009 | Wang et al. .......... 704/233 |
| 2009/0111507 | A1 * | 4/2009 | Chen .......... 455/550.1 |
| 2009/0154715 | A1 * | 6/2009 | Lyon et al. .......... 381/59 |
| 2010/0046770 | A1 * | 2/2010 | Chan et al. .......... 381/92 |
| 2010/0098266 | A1 * | 4/2010 | Mukund et al. .......... 381/94.7 |
| 2011/0106533 | A1 * | 5/2011 | Yu .......... 704/233 |

OTHER PUBLICATIONS

Boll, Steven F., "Suppression of Acoustic Noise in Speech Using Spectral Subtraction", IEEE Transactions on Acoustics, Speech, and Signal Porcessing, vol. ASSP-27, No. 2, Apr. 1979.

International Search Report mailed Jun. 30, 2011, in application serial No. PCT/US2010/026886, in the name of Harris Corporation.

* cited by examiner

NOISE ERROR AMPLITUDE REDUCTION

BACKGROUND OF THE INVENTION

1. Statement of the Technical Field

The invention concerns noise error amplitude reduction systems. More particularly, the invention concerns noise error amplitude reduction systems and methods for noise error amplitude reduction.

2. Description of the Related Art

In many communication systems, various noise cancellation techniques have been employed to reduce or eliminate unwanted sound from audio signals received at one or more microphones. Some conventional noise cancellation techniques generally use hardware and/or software for analyzing received audio waveforms for background aural or non-aural noise. The background non-aural noise typically degrades analog and digital voice. Non-aural noise can include, but is not limited to, diesel engines, sirens, helicopter noise, water spray and car noise. Subsequent to completion of the audio waveform analysis, a polarization reversed waveform is generated to cancel a background noise waveform from a received audio waveform. The polarization reversed waveform has an identical or directly proportional amplitude to the background noise waveform. The polarization reversed waveform is combined with the received audio signal thereby creating destructive interference. As a result of the destructive interference, an amplitude of the background noise waveform is reduced.

Despite the advantages of the conventional noise cancellation technique, it suffers from certain drawbacks. For example, the conventional noise cancellation technique does little to reduce the noise contamination in a severe or non-stationary acoustic noise environment.

Other conventional noise cancellation techniques generally use hardware and/or software for performing higher order statistic noise suppression. One such higher order statistic noise suppression method is disclosed by Steven F. Boll in "Suppression of Acoustic Noise in Speech Using Spectral Subtraction", IEEE Transactions on Acoustics, Speech, and Signal Processing, VOL. ASSP-27, No. 2, April 1979. This spectral subtraction method comprises the systematic computation of the average spectra of a signal and a noise in some time interval and afterwards through the subtraction of both spectral representations. Spectral subtraction assumes (i) a signal is contaminated by a broadband additive noise, (ii) a considered noise is locally stationary or slowly varying in short intervals of time, (iii) the expected value of a noise estimate during an analysis is equal to the value of the noise estimate during a noise reduction process, and (iv) the phase of a noisy, pre-processed and noise reduced, post-processed signal remains the same.

Despite the advantages of the conventional higher order statistic noise suppression method, it suffers from certain drawbacks. For example, the conventional higher order statistic noise suppression method encounters difficulties when tracking a ramping noise source. The conventional higher order statistic noise suppression method also does little to reduce the noise contamination in a ramping, severe or non-stationary acoustic noise environment.

Other conventional noise cancellation techniques use a plurality of microphones to improve speech quality of an audio signal. For example, one such conventional multi-microphone noise cancellation technique is described in the following document B. Widrow, R. C. Goodlin, et al., *Adaptive Noise Cancelling: Principles and Applications*, Proceedings of the IEEE, vol. 63, pp. 1692-1716, December 1975.

This conventional multi-microphone noise cancellation technique uses two (2) microphones to improve speech quality of an audio signal. A first one of the microphones receives a "primary" input containing a corrupted signal. A second one of the microphones receives a "reference" input containing noise correlated in some unknown way to the noise of the corrupted signal. The "reference" input is adaptively filtered and subtracted from the "primary" input to obtain a signal estimate.

Despite the advantages of the multi-microphone noise cancellation technique, it suffers from certain drawbacks. For example, analog voice is typically severely degraded by high levels of background non-aural noise. Although the conventional noise cancellation techniques reduce the amplitude of a background non-aural waveform contained in an audio signal input, the amount of the amplitude reduction is insufficient for certain applications, such as military applications, law enforcement applications and emergency response applications.

In view of the forgoing, there is a need in the art for a system and method to improve the intelligibility and quality of speech in the presence of high levels of background noise. There is also a need in the art for a system and method to improve the intelligibility and quality of speech in the presence of non-stationary background noise.

SUMMARY OF THE INVENTION

Embodiments of the present invention concern methods for noise error amplitude reduction. The method embodiments generally involve configuring a first microphone system and a second microphone system so that far field sound originating in a far field environment relative to the first and second microphone systems produces a difference in sound signal amplitude at the first and second microphone systems. The difference has a known range of values. The method embodiments also involve dynamically identifying the far field sound based on the difference. The identifying step comprises determining if the difference falls within the known range of values. The method embodiments further involve automatically reducing substantially to zero a gain applied to the far field sound responsive to the identifying step.

The reducing step comprises dynamically modifying the sound signal amplitude level for at least one component of the far field sound detected by the first microphone system. The dynamically modifying step further comprises setting the sound signal amplitude level for the component to be substantially equal to the sound signal amplitude of a corresponding component of the far field sound detected by the second microphone system. A gain applied to the component is determined based on a comparison of the relative sound signal amplitude level for the component and the corresponding component. The gain value is selected for the output audio signal based on a ratio of the sound signal amplitude level for the component and the corresponding component. The gain value is set to zero if the sound signal amplitude level for the component and the corresponding component are approximately equal.

The first microphone system and second microphone system are configured so that near field sound originating in a near field environment relative to the first and second microphone systems produces a second difference in the sound signal amplitude at the first and second microphone systems exclusive of the known range of values. The far field environment comprises locations at least three feet distant from the first and second microphone systems. The microphone configuration is provided by selecting at least one parameter of a first microphone associated with the first microphone system and a second microphone associated with the second microphone system. The parameter is selected from the group consisting of a distance between the first and second microphone, a microphone field pattern, a microphone orientation, and acoustic feed system.

Embodiments of the present invention also concern noise error amplitude reduction systems implementing the above described method embodiments. The system embodiments comprise the first microphone system, the second microphone system and at least one signal processing device. The first and second microphone systems are configured so that far field sound originating in a far field environment relative to the first and second microphone systems produces a difference in sound signal amplitude at the first and second microphone systems. The difference has a known range of values. The signal processing device is configured to dynamically identify the far field sound based on the difference. If the far field noise is identified, then the signal processing device is also configured to automatically reduce substantially to zero a gain applied to the far field sound.

BRIEF DESCRIPTION OF THE DRAWINGS

Embodiments will be described with reference to the following drawing figures, in which like numerals represent like items throughout the figures, and in which.

DETAILED DESCRIPTION

Figure 1A:
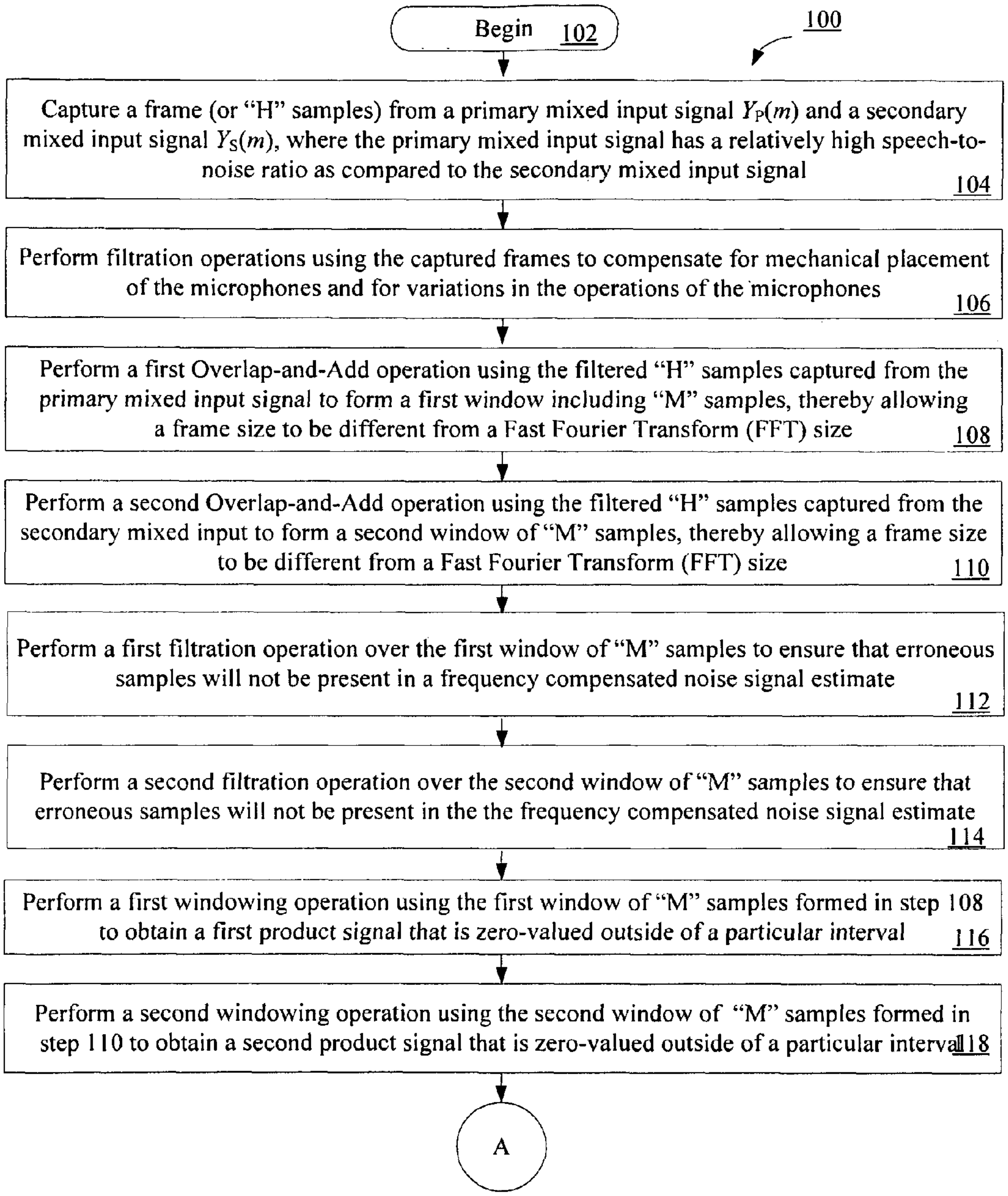
FIGS. 1A-1C collectively provide a flow diagram of an exemplary method for noise error amplitude reduction that is useful for understanding the present invention.

The present invention is described with reference to the attached figures, wherein like reference numbers are used throughout the figures to designate similar or equivalent elements. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. In other instances, well-known structures or operation are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

Embodiments of the present invention generally involve implementing systems and methods for noise error amplitude reduction. The method embodiments of the present invention overcome certain drawbacks of conventional noise error reduction techniques. For example, the method embodiments of the present invention provide a higher quality of speech in the presence of high levels of background noise as compared to conventional methods for noise error amplitude reduction. Also, the method embodiments of the present invention provide a higher quality of speech in the presence of non-stationary background noise as compared to conventional methods for noise error amplitude reduction.

The method embodiments of the present invention will be described in detail below in relation to FIGS. 1A-1C. However, it should be emphasized that the method embodiments implement modified spectral subtraction techniques for noise error amplitude reduction. The method embodiments produce a noise signal estimate from a noise source rather than from one or more incoming speech sources (as done in conventional spectral subtraction techniques). In this regard, the method embodiments generally involve receiving at least one primary mixed input signal and at least one secondary mixed input signal. The primary mixed input signal has a higher speech-to-noise ratio as compared to the secondary mixed input signal. A plurality of samples are produced by processing the secondary mixed input signal. The samples represent a Frequency Compensated Noise Signal Estimate (FCNSE) at different sample times. Thereafter, the FCNSE samples are used to reduce the amplitude of a noise waveform contained in the primary mixed input signal.

More particularly, the method embodiments involve receiving at least one primary mixed input signal at a first microphone system and at least one secondary mixed input signal at a second microphone system. The second microphone system is spaced a distance from the first microphone system. The microphone systems can be configured so that a ratio between a first signal level of far field noise arriving at the first microphone and a second signal level of far field noise arriving at the second microphone falls within a pre-defined range. For example, the distance between the microphone systems can be selected so that the ratio falls within the pre-defined range. The secondary mixed input signal has a lower speech-to-noise ratio as compared to the primary mixed input signal. The secondary mixed input signal is processed at a processor to produce the FCNSE. The primary mixed input signal is processed at the processor to reduce sample amplitudes of a noise waveform contained therein. The sample amplitudes are reduced using the FCNSE.

The FCNSE is generated by evaluating a magnitude level of the primary and secondary mixed input signal to identify far field noise components contained therein. This evaluation can involve comparing the magnitude of the secondary mixed input signal to the magnitude level of the primary mixed input signal. The magnitude of the secondary mixed input signal is compared to the magnitude level of the primary mixed input signal for determining if the magnitude levels satisfy a power ratio. The values of the far field noise components of the secondary mixed input signal are set equal to the far field noise components of the primary mixed input signal if the far field noise components fall within the pre-defined range. A least means squares algorithm is used to determine an average value for far field noise effects occurring at the first and second microphone systems.

The method embodiments of the present invention can be used in a variety of applications. For example, the method embodiments can be used in communication applications and voice recording applications. An exemplary communications device implementing a method embodiment of the present invention will be described in detail below in relation to FIGS. 2-6.

Method for Noise Error Amplitude Reduction

Figure 1B:
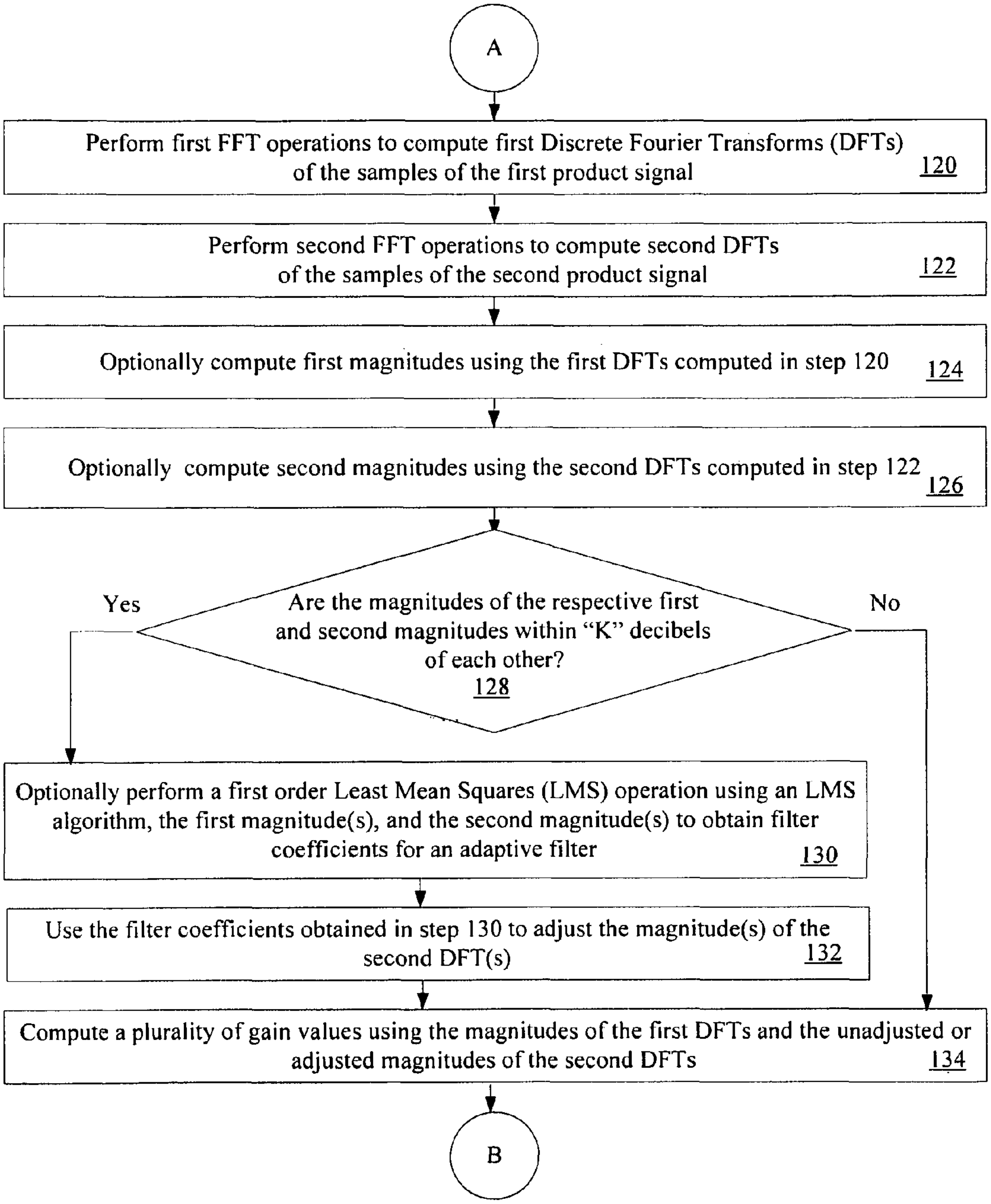
Figure 1C:
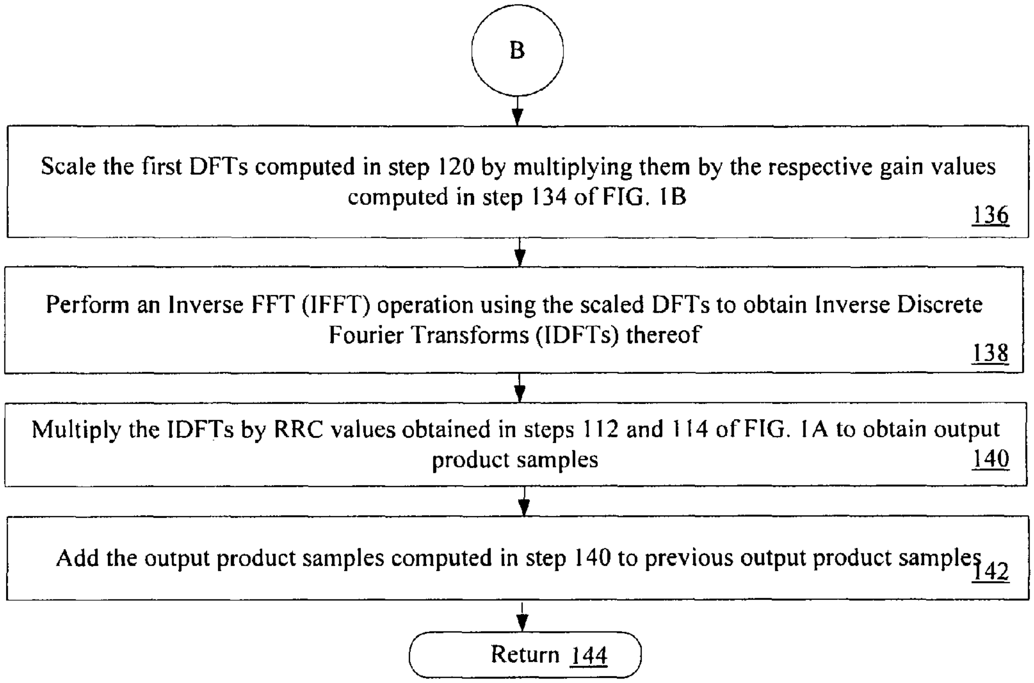

Referring now to FIGS. 1A-1C, there is provided an exemplary method 100 for noise error amplitude reduction that is useful for understanding the present invention. The goal of method 100 is: (a) to equalize a noise microphone signal input to match the phase and frequency response of a primary microphone input; (b) to adjust amplitude levels to exactly cancel the noise in the primary microphone input in the time domain; and (c) to zero filter taps that are "insignificant" so that audio Signal-to-Noise Ratio (SNR) is not degraded by a filtering process. Zeroing weak filter taps results in a better overall noise cancellation solution with improved speech SNR. The phrase "filter taps", as used herein, refers to the terms on the right-hand side of a mathematical equation defining how an input signal of a filter is related to an output signal of the filter. For example, if the mathematical equation $y[n]=b_0x[n]+b_1x[n-1]+\ldots+b_Nx[n-N]$ defines how an input signal of an $N^{th}$-order filter is related to an output signal of the an $N^{th}$-order filter, then the (N+1) terms on the right-hand side represent the filter taps.

As shown in FIG. 1A, method 100 begins with step 102 and continues with step 104. In step 104, a first frame of "H" samples is captured from a primary mixed input signal. "H" is an integer, such as one hundred and sixty (160). The primary mixed input signal can be, but is not limited to, a signal received at a first microphone and/or processed by front end hardware of a noise error amplitude reduction system. The front end hardware can include, but is not limited to, Analog-to-Digital Convertors (ADCs), filters, and amplifiers. Step 104 also involves capturing a second frame of "H" samples from a secondary mixed input signal. The secondary mixed input signal can be, but is not limited to, a signal that is received at a second microphone and/or processed by the front end hardware of the noise error amplitude reduction systems. The second microphone can be spaced a distance from the first microphone. The microphones can be configured so that a ratio between a first signal level of far field noise arriving at the first microphone and a second signal level of far field noise arriving at the first microphone falls within a pre-defined range (e.g., +/−0.3 dB). For example, the distance between the microphones can be configured so that ratio falls within the pre-defined range. Alternatively or additionally, one or more other parameters can be selected so that a ratio between a first signal level of far field noise arriving at the first microphone and a second signal level of far field noise arriving at the first microphone falls within a pre-defined range (e.g., +/−0.3 dB). The other parameters can be selected from the group consisting of a microphone field pattern, a microphone orientation, and acoustic feed system. The far field sound can be, but is not limited to, sound emanating from a source residing a distance of greater than three (3) or six (6) feet from the communication device 200.

The primary mixed input signal can be defined by the following mathematical equation (1). The secondary mixed input signal can be defined by the following mathematical equation (2).

$$Y_P(m)=x_P(m)+n_P(m) \tag{1}$$

$$Y_S(m)=x_S(m)+n_S(m) \tag{2}$$

where $Y_P(m)$ represents the primary mixed input signal. $x_P(m)$ is a speech waveform contained in the primary mixed input signal. $n_P(m)$ is a noise waveform contained in the primary mixed input signal. $Y_S(m)$ represents the secondary mixed input signal. $x_S(m)$ is a speech waveform contained in the secondary mixed input signal. $n_S(m)$ is a noise waveform contained in the secondary mixed input signal. The primary mixed input signal $Y_P(m)$ has a relatively high speech-to-noise ratio as compared to the speech-to-noise ratio of the secondary mixed input signal $Y_S(m)$.

After capturing a frame of "H" samples from the primary and secondary mixed input signals, the method 100 continues with step 106. In step 106, filtration operations are performed. Each filtration operation uses a respective one of the captured first and second frames of "H" samples. The filtration operations are performed to compensate for mechanical placement of the microphones on an object (e.g., a communications device). The filtration operations are also performed to compensate for variations in the operations of the microphones.

Each filtration operation can be implemented in hardware and/or software. For example, each filtration operation can be implemented via an FIR filter. The FIR filter is a sampled data filter characterized by its impulse response. The FIR filter generates a discrete time sequence which is the convolution of the impulse response and an input discrete time input defined by a frame of samples. The relationship between the input samples and the output samples of the FIR filter is defined by the following mathematical equation (3).

$$V_o[n]=A_0V_i[n]+A_1V_i[n-1]+A_2V_i[n-2]+\ldots+A_{N-1}V_i[n-N+1] \tag{3}$$

where $V_o[n]$ represents the output samples of the FIR filter. $A_0, A_1, A_2, \ldots A_{N-1}$ represent filter tap weights. N is the number of filter taps. N is an indication of the amount of memory required to implement the FIR filter, the number of calculations required to implement the FIR filter, and the amount of "filtering" the filter can provide. $V_i[n]$, $V_i[n-1]$, $V_i[n-2], \ldots, V_i[n-N+1]$ each represent input samples of the FIR filter. In the FIR filter, there is no feedback, and thus it is an all zero (0) filter. The phrase "all zero (0) filter", as used herein, means that the response of an FIR filter is shaped by placement of transmission zeros (0s) in a frequency domain.

Referring again to FIG. 1A, the method 100 continues with steps 108 and 110. In step 108, a first Overlap-and-Add operation is performed using the "H" samples captured from the primary mixed input signal $Y_P(m)$ to form a first window of "M" samples. In step 110, a second Overlap-and-Add operation is performed using the "H" samples captured from the secondary mixed input signal $Y_S(m)$ to form a second window of "M" samples. The first and second Overlap-and-Add operations allow a frame size to be different from a Fast Fourier Transform (FFT) size. During each Overlap-and-Add operation, at least a portion of the "H" samples captured from the input signal $Y_P(m)$ or $Y_S(m)$ may be overlapped and added with samples from a previous frame of the signal. Alternatively or additionally, one or more samples from a previous frame of the signal $Y_P(m)$ or $Y_S(m)$ may be appended to the front of the frame of "H" samples captured in step 104.

Referring again to FIG. 1A, the method 100 continues with steps 112 and 114. In step 112, a first filtration operation is performed over the first window of "M" samples. The first filtration operation is performed to ensure that erroneous samples will not be present in the FCNSE. In step 110, a second filtration operation is performed over the window including "M" samples of the secondary mixed input signal $Y_S(m)$. The second filtration operation is performed to ensure that erroneous samples will not be present in an estimate of the FCNSE. "M" is an integer, such as two hundred fifty-six (256).

The first and second filtration operations can be implemented in hardware and/or software. For example, the first and second filtration operation are implement via RRC filters. In such a scenario, each RRC filter is configured for pulse shaping of a signal. The frequency response of each RRC filter can generally be defined by the following mathematical equations (4)-(6).

$$F(\omega)=1 \text{ for } \omega<\omega_c(1-\alpha) \quad (4)$$

$$F(\omega)=0 \text{ for } \omega>\omega_c(1-\alpha) \quad (5)$$

$$F(\omega)=\text{sqrt}[(1+\cos((\pi(\omega-\omega_c(1-\alpha)))/2\alpha\omega_c))/2] \text{ for } \omega_c(1-\alpha)<\omega<\omega_c(1+\alpha) \quad (6)$$

where F(ω) represents the frequency response of an RRC filter. ω represents a radian frequency. $\omega_c$ represents a carrier frequency. α represents a roll off factor constant. Embodiments of the present invention are not limited to RRC filters having the above defined frequency response.

Referring again to FIG. 1A, the method 100 continues with step 116 and 118. In step 116, a first windowing operation is performed using the first window of "M" samples formed in step 108 to obtain a first product signal. The first product signal is zero-valued outside of a particular interval. Similarly, step 118 involves performing a second windowing operation using the second window of "M" samples to obtain a second product signal. The second product signal is zero-valued outside of a particular interval. Each windowing operation generally involves multiplying "M" samples by a "window" function thereby producing the first or second product signal. The first and second windowing operations are performed so that accurate FFT representations of the "M" samples are obtained during subsequent FFT operations.

After completing step 118, the method 100 continues with step 120 of FIG. 1B. Step 120 involves performing first FFT operations for computing first Discrete Fourier Transforms (DFTs) using the first product signal. The first FFT operation generally involves applying a Fast Fourier transform to the real and imaginary components of the first product signal samples. A next step 122 involves performing second FFT operations for computing second DFTs using the second product signal. The second FFT operation generally involves applying a Fast Fourier transform to the real and imaginary components of the second product signal samples.

Upon computing the first and second DFTs, step 124 and 126 are performed. In step 124, first magnitudes are computed using the first DFTs computed in step 120. Second magnitudes are computed in step 126 using the second DFTs computed in step 122. The first and second magnitude computations can generally be defined by the following mathematic equation (7).

$$\text{magnitude}[i]=\text{sqrt}(\text{real}[i]\cdot\text{real}[i]+\text{imag}[i]\cdot\text{imag}[i]) \quad (7)$$

where magnitude[i] represents a first or second magnitude. real[i] represents the real components of a first or second DFT. imag[i] represents an imaginary component of a first or second DFT. Embodiments of the present invention are not limited in this regard. For example, steps 124 and/or 126 can alternatively or additionally involve obtaining pre-stored magnitude approximation values from a memory device. Steps 124 and/or 126 can also alternatively or additionally involve computing magnitude approximation values rather than actual magnitude values as shown in FIG. 1B.

Thereafter, a decision step 128 is performed for determining if signal inaccuracies occurred at one or more microphones and/or for determining the differences in far field noise effects occurring at the first and second microphones. This determination can be made by evaluating a relative magnitude level of the primary and secondary mixed input signal to identify far field noise components contained therein. As shown in FIG. 1B, signal inaccuracies and far field noise effects exist if magnitudes of respective first and second magnitudes are within "K" decibels (e.g., within +/−6 dB) of each other. If the magnitudes of the respective first and second magnitudes are not within "K" decibels of each other [128:NO], then method 100 continues with step 134. Step 134 will be described below. If the magnitudes of the respective first and second magnitudes are within "K" decibels of each other [128:NO], then method 100 continues with step 130.

Step 130 involves optionally performing a first order Least Mean Squares (LMS) operation using an LMS algorithm, the first magnitude(s), and the second magnitude(s). The first order LMS operation is generally performed to compensate for signal inaccuracies occurring in the microphones and to drive far field noise effects occurring at the first and second microphones to zero (i.e., to facilitate the elimination of a noise waveform from the primary mixed input signal). The LMS operation determines an average value for far field noise effects occurring at the first and second microphone systems. The first order LMS operation is further performed to adjust an estimated noise level for level differences in signal levels between fair field noise levels in the two (2) signal $Y_P(m)$ and $Y_S(m)$ channels. In this regard, the first order LMS operation is performed to find filter coefficients for an adaptive filter that relate to producing a least mean squares of an error signal (i.e., the difference between the desired signal and the actual signal). LMS algorithms are well known to those having ordinary skill in the art, and therefore will not be described herein. Embodiments of the present invention are not limited in this regard. For example, if a Wiener filter is used to produce an error signal (instead of an adaptive filter), then the first order LMS operation need not be performed. Also, the LMS operation need not be performed if frequency compensation of the adaptive filter is to be performed automatically using pre-stored filter coefficients.

Upon completing step 130, step 132 is performed to frequency compensate for any signal inaccuracies that occurred at the microphones. Step 132 is also performed to drive far field noise effects occurring at the first and second microphones to zero (i.e., to facilitate the elimination of a noise waveform from the primary mixed input signal) by setting the values of the far field noise components of the secondary mixed input signal equal to the far field noise components of the primary mixed input signal. Accordingly, step 132 involves using the filter coefficients to adjust the second magnitude(s). Step 132 can be implemented in hardware and/or software. For example, the magnitude(s) of the second DFT(s) can be adjusted at an adaptive filter using the filter coefficients computed in step 130. Embodiments of the present invention are not limited in this regard.

Subsequent to completing step 128 or steps 128-132, step 134 of FIG. 1B and step 136 of FIG. 1C are performed for reducing the amplitude of the noise waveform $n_P(m)$ of the primary mixed input signal $Y_P(m)$ or eliminating the noise waveform $n_P(m)$ from the primary mixed input signal $Y_P(m)$. In a step 134, a plurality of gain values are computed using the first magnitudes computed in step 120 for the first DFTs. The gain values are also computed using the second magnitude(s) computed in step 122 for the second DFTs and/or the adjusted magnitude(s) generated in step 132.

The gain value computations can generally be defined by the following mathematical equation (8).

$$\text{gain}[i]=1.0-\text{noise\_mag}[i]\div\text{primary\_mag}[i] \quad (8)$$

where gain[i] represents a gain value. noise_mag[i] represent a magnitude of a second DFT computed in step 122 or an adjusted magnitude of the second DFT generated in step 132. primary_mag[i] represents a magnitude for the a first DFT computed in step 120.

Step 134 can also involve limiting the gain values so that they fall within a pre-selected range of values (e.g., values falling within the range of 0.0 to 1.0, inclusive of 0.0 and 1.0). Such gain value limiting operations can generally be defined by the following "if-else" statement.

if (gain[i]>$psv_1$), then gain[i]=$psv_1$;

else if (gain[i]<$psv_2$), then gain[i]=$psv_2$.

$psv_1$ represents a first pre-selected value defining a high end of a range of gain values. $psv_2$ represents a second pre-selected value defining a low end of a range of gain values. Embodiments of the present invention are not limited in this regard.

In step 136 of FIG. 1C, scaling operations is performed to scale the first DFTs computed in step 120. The scaling operations involves using the gain values computed in step 134 of FIG. 1B. The scaling operations can generally be defined by mathematical equations (9) and (10).

$$x'(i).\text{real}=x(i).\text{real}\cdot\text{gain}[i] \quad (9)$$

$$x'(i).\text{imag}=x(i).\text{imag}\cdot\text{gain}[i] \quad (10)$$

where x'(i).real represents a real component of a scaled first DFT. x'(i).imag represents an imaginary component of the scaled first DFT. x(i).real represents a real component of a first DFT computed in step 120. x(i).imag represents an imaginary component of the first DFT.

After completing step 136, the method 100 continues with step 138. In step 138, an Inverse FFT (IFFT) operation is performed using the scaled DFTs obtained in step 136. The IFFT operation is performed to reconstruct a noise reduced speech signal $X_P(m)$. The results of the IFFT operation are Inverse Discrete Fourier transforms of the scaled DFTs. Subsequently, step 140 is performed where the samples of the noise reduced speech signal $X_P(m)$ are multiplied by the RRC values obtained in steps 112 and 114 of FIG. 1A. The outputs of the multiplication operations illustrate an anti-symmetric filter shape between the current frame samples and the previous frame samples overlapped and added thereto in steps 108 and 110 of FIG. 1A. The results of the multiplication operations performed in step 140 are herein referred to as an output product samples. The output product samples computed in step 140 are then added to previous output product samples in step 142. In effect, the fidelity of the original samples are restored. Thereafter, step 144 is performed where the method 100 returns to step 104 or subsequent processing is resumed.

Exemplary Communications Device Implementing Method 100

Figure 2:
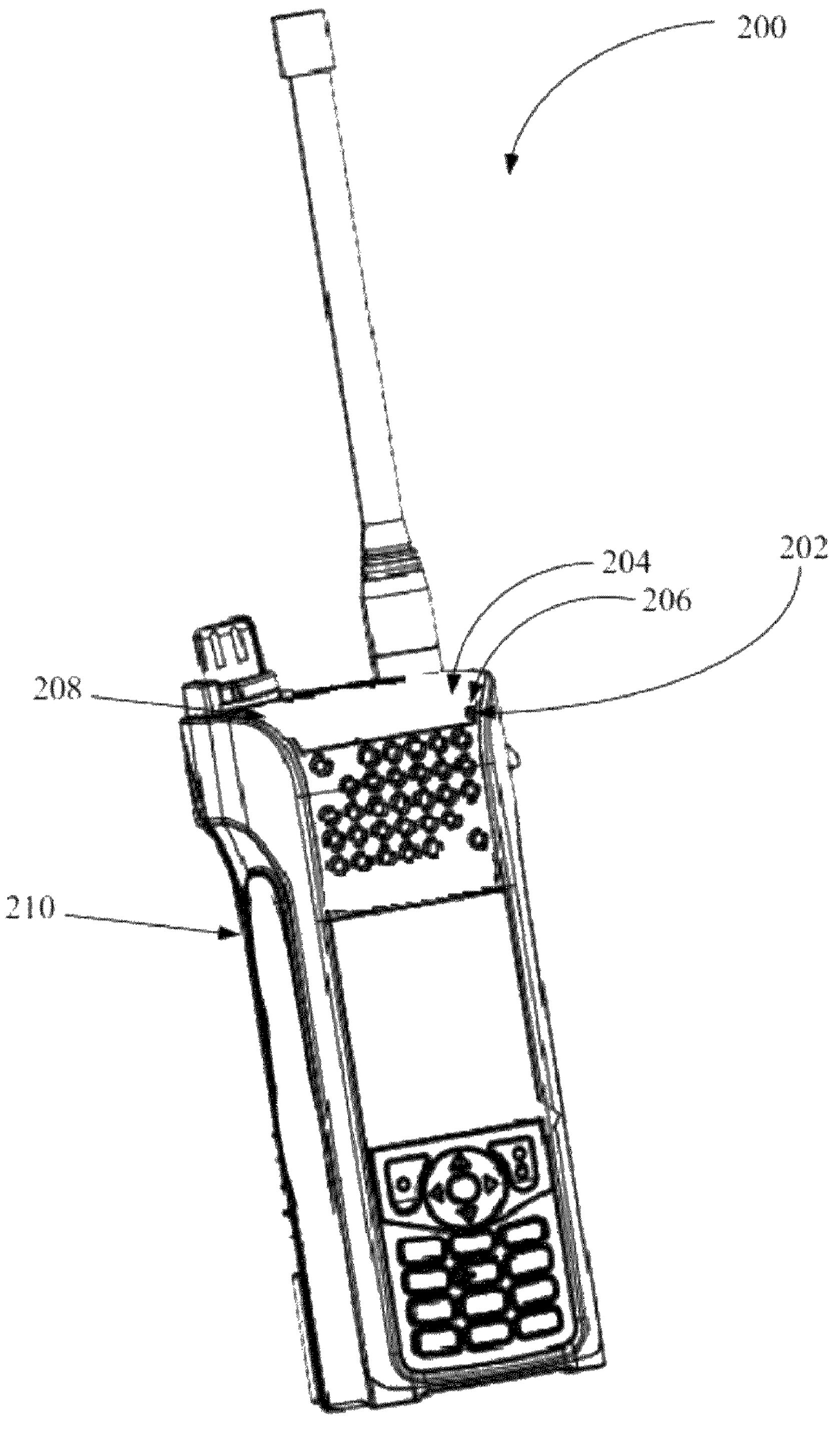
FIG. 2 is a front perspective view of an exemplary communication device implementing the method of FIGS. 1A-1C that is useful for understanding the present invention.
Figure 3:
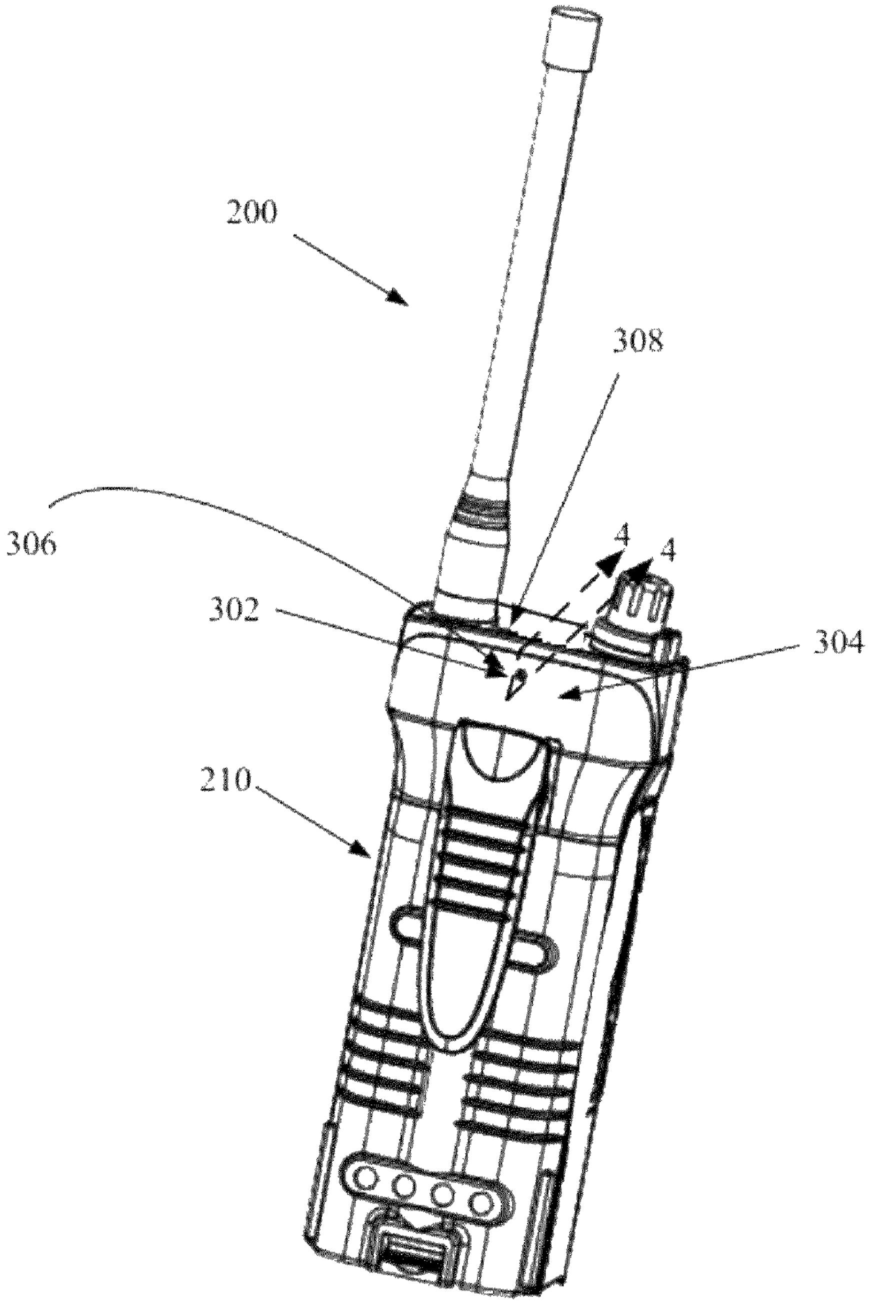
FIG. 3 is a back perspective view of the exemplary communication device shown in FIG. 2.

Referring now to FIGS. 2-3, there are provided front and back perspective views of an exemplary communication device 200 implementing method 100 of FIGS. 1A-1C. The communication device 200 can be, but is not limited to, a radio, a mobile phone, a cellular phone, or other wireless communication device.

According to embodiments of the present invention, communication device 200 is a land mobile radio system intended for use by terrestrial users in vehicles (mobiles) or on foot (portables). Such land mobile radio systems are typically used by military organizations, emergency first responder organizations, public works organizations, companies with large vehicle fleets, and companies with numerous field staff. The land mobile radio system can communicate in analog mode with legacy land mobile radio systems. The land mobile radio system can also communicate in either digital or analog mode with other land mobile radio systems. The land mobile radio system may be used in: (a) a "talk around" mode without any intervening equipment between two land mobile radio systems; (b) a conventional mode where two land mobile radio systems communicate through a repeater or base station without trunking; or (c) a trunked mode where traffic is automatically assigned to one or more voice channels by a repeater or base station. The land mobile radio system 200 can employ one or more encoders/decoders to encode/decode analog audio signals. The land mobile radio system can also employ various types of encryption schemes from encrypting data contained in audio signals. Embodiments of the present invention are not limited in this regard.

As shown in FIGS. 2-3, the communication device 200 comprises a first microphone 202 disposed on a front surface 204 thereof and a second microphone 302 disposed on a back surface 304 thereof. The microphones 202, 302 are arranged on the surfaces 204, 304 so as to be parallel with respect to each other. The presence of the noise waveform $x_S(m)$ in a signal generated by the second microphone 302 is controlled by its "audio" distance from the first microphone 202. Accordingly, each microphone 202, 302 can be disposed a distance from a peripheral edge 208, 308 of a respective surface 204, 304. The distance can be selected in accordance with a particular application. For example, microphone 202 can be disposed ten (10) millimeters from the peripheral edge 208, 308 of surface 204. Microphone 302 can be disposed four (4) millimeters from the peripheral edge 208, 308 of surface 304. Embodiments of the present invention are not limited in this regard.

According to embodiments of the present invention. each of the microphones 202, 302 is a MicroElectroMechanical System (MEMS) based microphone. More particularly, each of the microphones 202, 302 is a silicone MEMS microphone having a part number SMM310 which is available from Infineon Technologies North America Corporation of Milpitas, Calif. Embodiments of the present invention are not limited in this regard.

The first and second microphones 202, 302 are placed at locations on surfaces 204, 304 of the communication device 200 that are advantageous to noise cancellation. In this regard, it should be understood that the microphones 202, 302 are located on surfaces 204, 304 such that they output the same signal for far field sound. For example, if the microphones 202 and 302 are spaced four (4) inches from each other, then an interfering signal representing sound emanating from a sound source located six (6) feet from the communication device 200 will exhibit a power (or intensity) difference between the microphones 204, 304 of less than half a decibel (0.5 dB). The far field sound is generally the background noise that is to be removed from the primary mixed input signal $Y_P(m)$. According to embodiments of the present invention, the microphone arrangement shown in FIGS. 2-3 is selected so that far field sound is sound emanating from a source residing a distance of greater than three (3) or six (6) feet from the communication device 200. Embodiments of the present invention are not limited in this regard.

The microphones 202, 302 are also located on surfaces 204, 304 such that microphone 202 has a higher level signal than the microphone 302 for near field sound. For example, the microphones 202, 302 are located on surfaces 204, 304 such that they are spaced four (4) inches from each other. If sound is emanating from a source located one (1) inch from the microphone 202 and four (4) inches from the microphone 302, then a difference between power (or intensity) of a signal representing the sound and generated at the microphones 202, 302 is twelve decibels (12 dB). The near field sound is generally the voice of a user. According to embodiments of the present invention, the near field sound is sound occurring a distance of less than six (6) inches from the communication device 200. Embodiments of the present invention are not limited in this regard.

Figure 4:
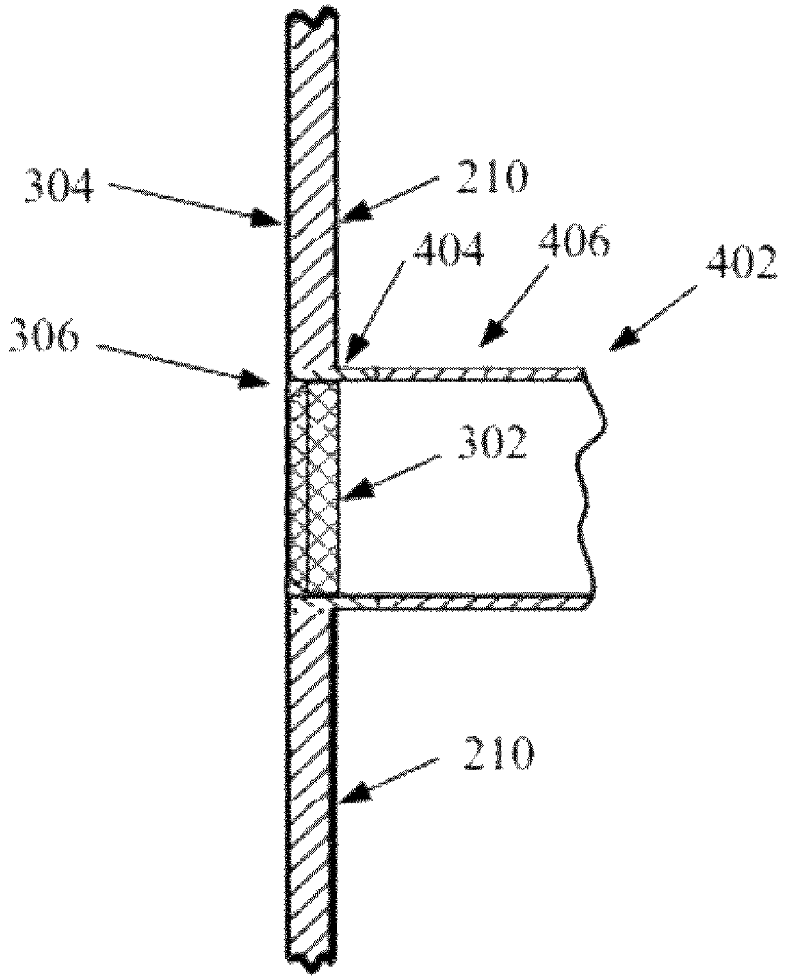
FIG. 4 is a cross-sectional view of a portion of the exemplary communication device taken along line 4-4 of FIG. 3.

The microphone arrangement shown in FIGS. 2-4 can accentuate the difference between near and far field sounds. Accordingly, the microphones 202, 302 are made directional so that far field sound is reduced in relation to near field sound in one (1) or more directions. The microphone 202, 302 directionality is achieved by disposing each of the microphones 202, 302 in a tube 402 inserted into a through hole 206, 306 formed in a surface 204, 304 of the communication device's 200 housing 210. The tube 402 can have any size (e.g., 2 mm) selected in accordance with a particular application. The tube 402 can be made from any material selected in accordance with a particular application, such as plastic, metal and/or rubber. Embodiments of the present invention are not limited in this regard. For example, the microphone 202, 302 directionality can be achieved using acoustic phased arrays.

According to the embodiment shown in FIG. 3, the hole 206, 306 in which the tube 402 is inserted is shaped and/or filled with a material to reduce the effects of wind noise and "pop" from close speech. The tube 402 includes a first portion 406 formed from plastic or metal. The tube 402 also includes a second portion 404 formed of rubber. The second portion 404 provides an environmental seal around the microphone 202, 302 at locations where it passes through the housing 210 of the communication device 200. The environmental seal prevents moisture from seeping around the microphone 202, 302 and into the communication device 200. The second portion 404 also provides an acoustic seal around the microphone 202, 302 at locations where it passes through the housing 210 of the communication device 200. The acoustic seal prevents sound from seeping into and out of the communication device 200. In effect, the acoustic seal ensures that there are no shorter acoustic paths through the radio which will cause a reduction of performance. The tube 402 ensures that the resonant point of the through hole 206, 306 is greater than a frequency range of interest. Embodiments of the present invention are not limited in this regard.

According to other embodiments of the present invention, the tube 402 is a single piece designed to avoid resonance which yields a band pass characteristic. Resonance is avoided by using a porous material in the tube 402 to break up the air flow. A surface finish is provided on the tube 402 that imposes friction on the layer of air touching a wall (not shown) thereof. Embodiments of the present invention are not limited in this regard.

Figure 5:
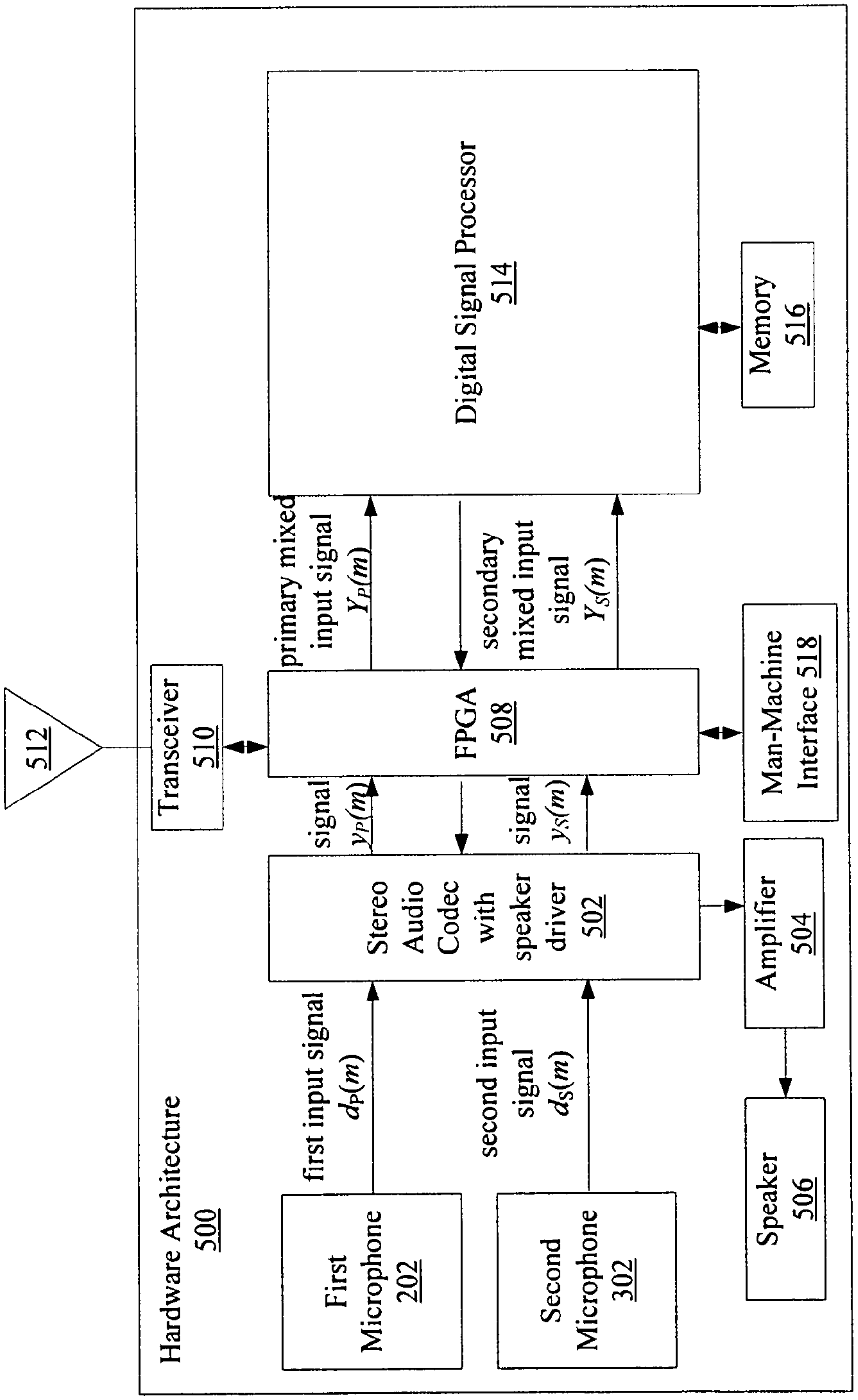
FIG. 5 is a block diagram illustrating an exemplary hardware architecture of the communication device shown in FIGS. 2-4 that is useful for understanding the present invention.

Referring now to FIG. 5, there is provided a block diagram of an exemplary hardware architecture 500 of the communication device 200. As shown in FIG. 5, the hardware architecture 500 comprises the first microphone 202 and the second microphone 302. The hardware architecture 500 also comprises a Stereo Audio Codec (SAC) 502 with a speaker driver, an amplifier 504, a speaker 506, a Field Programmable Gate Array (FPGA) 508, a transceiver 501, an antenna element 512, and a Man-Machine Interface (MMI) 518. The MMI 518 can include, but is not limited to, radio controls, on/off switches or buttons, a keypad, a display device, and a volume control. The hardware architecture 500 is further comprised of a Digital Signal Processor (DSP) 514 and a memory device 516.

The microphones 202, 302 are electrically connected to the SAC 502. The SAC 502 is generally configured to sample input signals coherently in time between the first and second input signal $d_P(m)$ and $d_S(m)$ channels. As such, the SAC 502 can include, but is not limited to, a plurality of ADCs that sample at the same sample rate (e.g., eight or more kilo Hertz). The SAC 502 can also include, but is not limited to, Digital-to-Analog Convertors (DACs), drivers for the speaker 506, amplifiers, and DSPs. The DSPs can be configured to perform equalization filtration functions, audio enhancement functions, microphone level control functions, and digital limiter functions. The DSPs can also include a phase lock loop for generating accurate audio sample rate clocks for the SAC 502. According to an embodiment of the present invention, the SAC 502 is a codec having a part number WAU8822 available from Nuvoton Technology Corporation America of San Jose, Calif. Embodiments of the present invention are not limited in this regard.

As shown in FIG. 5, the SAC 502 is electrically connected to the amplifier 504 and the FPGA 508. The amplifier 504 is generally configured to increase the amplitude of an audio signal received from the SAC 502. The amplifier 504 is also configured to communicate the amplified audio signal to the speaker 506. The speaker 506 is generally configured to convert the amplifier audio signal to sound. In this regard, the speaker 506 can include, but is not limited to, an electro acoustical transducer and filters.

The FPGA 508 is electrically connected to the SAC 502, the DSP 514, the MMI 518, and the transceiver 510. The FPGA 508 is generally configured to provide an interface between the components 502, 514, 518, 510. In this regard, the FPGA 508 is configured to receive signals $y_S(m)$ and $y_P(m)$ from the SAC 502, process the received signals, and forward the processed signals $Y_P(m)$ and $Y_S(m)$ to the DSP 514.

The DSP 514 generally implements method 100 described above in relation to FIGS. 1A-1C. As such, the DSP 514 is configured to receive the primary mixed input signal $Y_P(m)$ and the secondary mixed input signal $Y_S(m)$ from the FPGA 508. At the DSP 514, the primary mixed input signals $Y_P(m)$ is processed to reduce the amplitude of the noise waveform $n_P(m)$ contained therein or eliminate the noise waveform $n_P(m)$ therefrom. This processing can involve using the secondary mixed input signal $Y_S(m)$ in a modified spectral subtraction method. The DSP 514 is electrically connected to memory 516 so that it can write information thereto and read information therefrom. The DSP 514 will be described in detail below in relation to FIG. 6.

The transceiver 510 is generally a unit which contains both a receiver (not shown) and a transmitter (not shown). Accordingly, the transceiver 510 is configured to communicate signals to the antenna element 512 for communication to a base station, a communication center, or another communication device 200. The transceiver 510 is also configured to receive signals from the antenna element 512.

Figure 6:
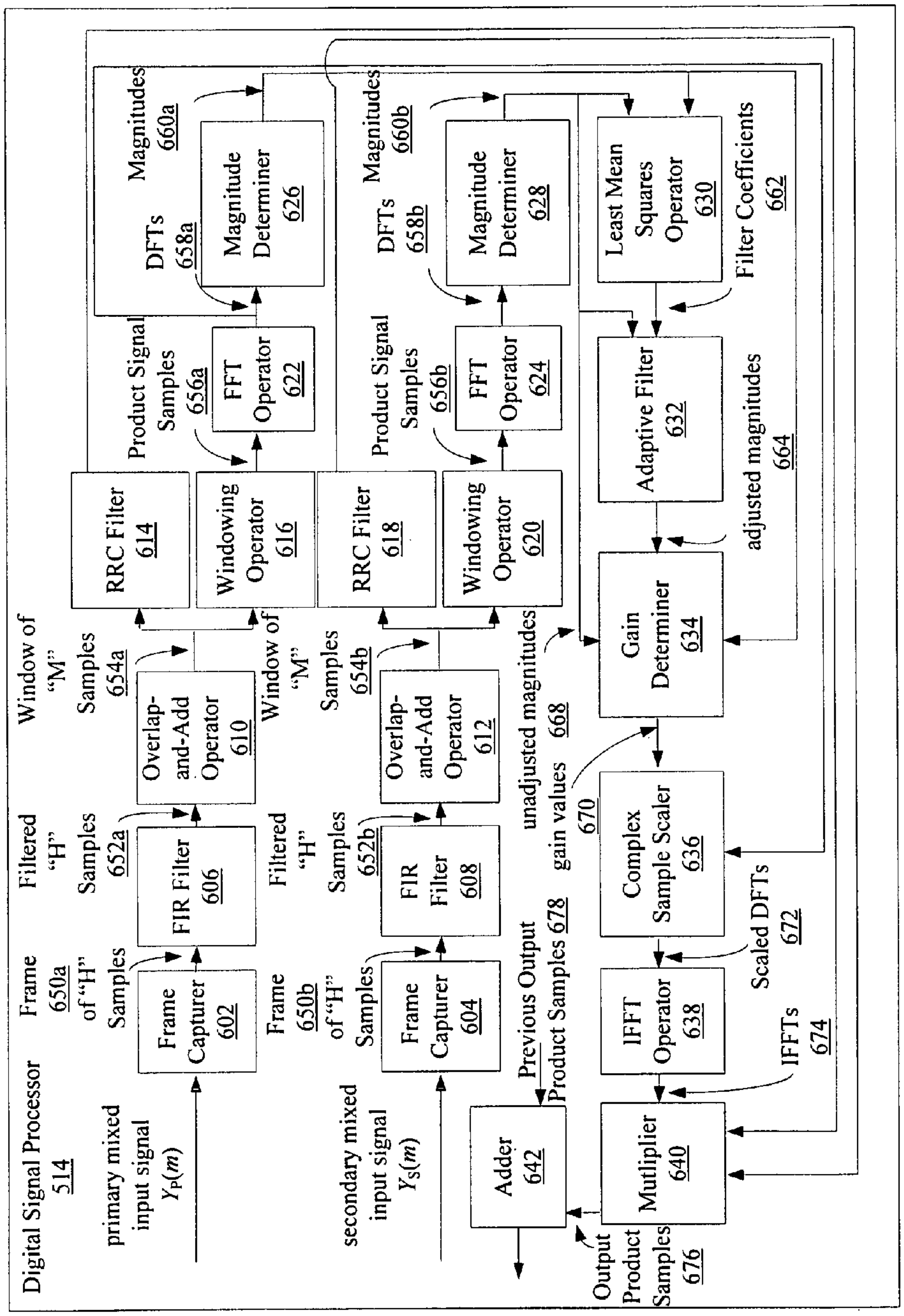
FIG. 6 is a more detailed block diagram of the Digital Signal Processor shown in FIG. 5 that is useful for understanding the present invention.

Referring now to FIG. 6, there is provided a more detailed block diagram of the DSP 514 shown in FIG. 5 that is useful for understanding the present invention. As noted above, the DSP 514 generally implements method 100 described above in relation to FIGS. 1A-1C. Accordingly, the DSP 514 comprises frame capturers 602, 604, FIR filters 606, 608, Overlap-and-Add (OA) operators 610, 612, RRC filters 614, 618, and windowing operators 616, 620. The DSP 514 also comprises FFT operators 622, 624, magnitude determiners 626, 628, an LMS operator 630, and an adaptive filter 632. The DSP 514 is further comprised of a gain determiner 634, a Complex Sample Scaler (CSS) 636, an IFFT operator 638, a multiplier 640, and an adder 642. Each of the components 602, 604, . . . , 642 shown in FIG. 6 can be implemented in hardware and/or software.

Each of the frame capturers 602, 604 is generally configured to capture a frame 650*a*, 650*b* of "H" samples from the primary mixed input signal $Y_P(m)$ or the secondary mixed input signal $Y_S(m)$. Each of the frame capturers 602, 604 is also configured to communicate the captured frame 650*a*, 650*b* of "H" samples to a respective FIR filter 606, 608. Each of the FIR filters 606, 608 is configured to filter the "H" samples from a respective frame 650*a*, 650*b*. The FIR filters 606, 608 are provided to compensate for mechanical placement of the microphones 202, 302. The FIR filters 606, 608 are also provided to compensate for variations in the operations of the microphones 202, 302. The FIR filters 606, 608 are also configured to communicate the filtered "H" samples 652*a*, 652*b* to a respective OA operator 610, 612. Each of the OA operators 610, 612 is configured to receive the filtered "H" samples 652*a*, 652*b* from an FIR filter 606, 608 and form a window of "M" samples using the filtered "H" samples 652*a*, 652*b*. Each of the windows of "M" samples 652*s*, 652*b* is formed by: (a) overlapping and adding at least a portion of the filtered "H" samples 652*a*, 652*b* with samples from a previous frame of the signal $Y_P(m)$ or $Y_S(m)$; and/or (b) appending the previous frame of the signal $Y_P(m)$ or $Y_S(m)$ to the front of the frame of the filtered "H" samples 652*a*, 652*b*.

The windows of "M" samples 654*a*, 654*b* are then communicated from the OA operators 610, 612 to the RRC filters 614, 618 and windowing operators 616, 620. Each of the RRC filters 614, 618 is configured to ensure that erroneous samples will not be present in the FCNSE. As such, the RRC filters 614, 618 perform RRC filtration operations over the windows of "M" samples 654*a*, 654*b*. The results of the filtration operations (also referred to herein as the "RRC" values") are communicated from the RRC filters 614, 618 to the multiplier 640. The RRC values facilitate the restoration of the fidelity of the original samples of the signal $Y_P(m)$.

Each of the windowing operators 616, 620 is configured to perform a windowing operation using a respective window of "M" samples 654*a*, 654*b*. The result of the windowing operation is a plurality of product signal samples 656*a* or 656*b*. The product signal samples 656*a*, 656*b* are communicated from the windowing operators 616, 620 to the FFT operators 622, 624, respectively. Each of the FFT operators 622, 624 is configured to compute DFTs 658*a*, 658*b* of respective product signal samples 656*a*, 656*b*. The DFTs 658*a*, 658*b* are communicated from the FFT operators 622, 624 to the magnitude determiners 626, 628, respectively. At the magnitude determiners 626, 628, the DFTs 658*a*, 658*b* are processed to determine magnitudes 660*a*, 660*b* thereof. The magnitudes 660*a*, 660*b* are communicated from the magnitude determiners 626, 628 to the gain determiner 634. The magnitudes 660*b* are also communicated to the LMS operator 630 and the adaptive filter 632.

The LMS operator 630 generates filter coefficients 662 for the adaptive filter 632. The filter coefficients 662 are generated using an LMS algorithm and the magnitudes 660*a*, 660*b*. LMS algorithms are well known to those having ordinary skill in the art, and therefore will not be described herein. However, any LMS algorithm can be used without limitation. At the adaptive filter 632, the magnitudes 600*b* are adjusted. The adjusted magnitudes 664 are communicated from the adaptive filter 632 to the gain determiner 634.

The gain determiner 634 is configured to compute a plurality of gain values 670. The gain value computations are defined above in relation to mathematical equation (9). The gain values 670 are computed using the magnitudes 660*a* and the unadjusted or adjusted magnitudes 660*b*, 664. If the powers of the primary mixed input signal $Y_P(m)$ and the secondary mixed input signal $Y_S(m)$ are within "K" decibels (e.g., 6 dB) of each other, then the gain values 670 are computed using the magnitudes 660*a* and the unadjusted magnitudes 664. However, if the powers of the primary mixed input signal $Y_P(m)$ and the secondary mixed input signal $Y_S(m)$ are not within "K" decibels (e.g., 6 dB) of each other, then the gain values 670 are computed using the magnitudes 660*a* and the adjusted magnitudes 660*b*. The gain values 670 can be limited so as to fall within a pre-selected range of values (e.g., values falling within the range of 0.0 to 1.0, inclusive of 0.0 and 1.0). The gain values are communicated from the gain determiner 634 to the CSS 636.

At the CSS 636, scaling operations are performed to scale the DFTs. The scaling operations generally involve multiplying the real and imaginary components of the DFTs by the gain values 670. The scaling operations are defined above in relation to mathematical equations (10) and (11). The scaled DFTs 672 are communicated from the CSS 636 to the IFFT operator 638. The IFFT operator 638 is configured to perform IFFT operations using the scaled DFTs 672. The results of the IFFT operations are IDFTs 674 of the scaled DFTs 672. The IDFTs 674 are communicated from the IFFT operator 638 to the multiplier 640. The multiplier 640 multiplies the IDFTs 674 by the RRC values received from the RRC filters 614, 618 to produce output product samples 676. The output product samples 676 are communicated from the multiplier 640 to the adder 642. At the adder 642, the output product samples 676 are added to previous output product samples 678. The output of the adder 642 is a plurality of signal samples representing the primary mixed input signal $Y_P(m)$ having reduced noise signal $n_P(m)$ amplitudes.

In light of the forgoing description of the invention, it should be recognized that the present invention can be realized in hardware, software, or a combination of hardware and software. A method for noise error amplitude reduction according to the present invention can be realized in a centralized fashion in one processing system, or in a distributed fashion where different elements are spread across several interconnected processing systems. Any kind of computer system, or other apparatus adapted for carrying out the methods described herein, is suited. A typical combination of hardware and software could be a general purpose computer processor, with a computer program that, when being loaded and executed, controls the computer processor such that it carries out the methods described herein. Of course, an application specific integrated circuit (ASIC), and/or a field programmable gate array (FPGA) could also be used to achieve a similar result.

Applicants present certain theoretical aspects above that are believed to be accurate that appear to explain observations made regarding embodiments of the invention. However, embodiments of the invention may be practiced without the theoretical aspects presented. Moreover, the theoretical aspects are presented with the understanding that Applicants do not seek to be bound by the theory presented.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments. Rather, the scope of the invention should be defined in accordance with the following claims and their equivalents.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The terminology used herein is for the purpose of describing particular embodiments only and is not intended to be limiting of the invention. As used herein, the singular forms “a”, “an” and “the” are intended to include the plural forms as well, unless the context clearly indicates otherwise. Furthermore, to the extent that the terms “including”, “includes”, “having”, “has”, “with”, or variants thereof are used in either the detailed description and/or the claims, such terms are intended to be inclusive in a manner similar to the term “comprising.”

The word “exemplary” is used herein to mean serving as an example, instance, or illustration. Any aspect or design described herein as “exemplary” is not necessarily to be construed as preferred or advantageous over other aspects or designs. Rather, use of the word exemplary is intended to present concepts in a concrete fashion. As used in this application, the term “or” is intended to mean an inclusive “or” rather than an exclusive “or”. That is, unless specified otherwise, or clear from context, “X employs A or B” is intended to mean any of the natural inclusive permutations. That is if, X employs A; X employs B; or X employs both A and B, then “X employs A or B” is satisfied under any of the foregoing instances.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

We claim:

1. A method for noise reduction, comprising:

receiving a primary mixed input signal at a first microphone system of a communication device and a second mixed input signal at a second microphone system of said communication device, said first and second microphone systems disposed at locations on said communication device so that far field sound originating in a far field environment relative to said first and second microphone systems produces a first difference in sound signal amplitude at said first and second microphone systems;

dynamically identifying a first far field sound component contained in said primary mixed input signal and a second far field sound component contained in said secondary mixed input signal based on said first difference, said first far field sound component having first magnitude values and said second far field sound component having second magnitude values;

generating adjusted magnitude values by setting said second magnitude values equal to said first magnitude values;

determining a plurality of gain values using said first magnitude values and said adjusted magnitude values; and automatically reducing said first far field sound component using said plurality of gain values.

2. The method according to claim 1, wherein said identifying step comprises determining if said first difference falls within a predefined range of values.

3. The method according to claim 1, wherein said reducing step comprises dynamically modifying said sound signal amplitude level for at least one first component of said far field sound detected by said first microphone system.

4. The method according to claim 3, wherein said component is a frequency component.

5. The method according to claim 1, wherein at least one of said plurality of gain values is determined based on a comparison of a relative sound signal amplitude level for said first far field sound component and said second far field sound component.

6. The method according to claim 1, wherein at least one of said plurality of gain values is selected based on a ratio of said sound signal amplitude level for said first far field sound component and said second far field sound component.

7. The method according to claim 6, further comprising setting at least one of said plurality of gain values to zero if said sound signal amplitude level for said first component and said second component are approximately equal.

8. The method according to claim 1, further comprising configuring said first microphone system and said second microphone system so that near field sound originating in a near field environment relative to said first and second microphone systems produces a second difference in said sound signal amplitude at said first and second microphone systems, said second difference different than said first difference.

9. The method according to claim 1, wherein said far field environment comprises locations at least three feet distant from said first and second microphone systems.

10. The method according to claim 1, further comprising selecting at least one parameter of a first microphone associated with said first microphone system and a second microphone associated with said second microphone system.

11. The method according to claim 10, wherein said parameter is selected from the group consisting of a distance between said first and second microphones, a microphone field pattern, a microphone orientation, and acoustic feed system.

12. A noise error amplitude reduction (“NEAR”) system, comprising:

a first microphone system configured to produce a primary mixed input signal;

a second microphone system configured to produce a secondary mixed input signal, where said first and second microphone systems are disposed at locations on a communication device so that far field sound originating in a far field environment relative to said first and second microphone systems produces a first difference in sound signal amplitude at said first and second microphone systems;

at least one signal processing device configured to dynamically identify a first far field sound component of said primary mixed input signal and a second far field sound component of said secondary mixed input signal based on said first difference, said first far field sound component having first magnitude values and said second far field sound component having second magnitude values, generating adjusted magnitude values by setting said second magnitude values equal to said first magnitude values, computing a plurality of gain values using said first magnitude values and said adjusted magnitude values, and automatically reduce said first far field sound component using said plurality of gain values.

13. The noise error amplitude reduction system according to claim 12, wherein said far field sound is identified by determining if said first difference falls within a predefined range of values.

14. The noise error amplitude reduction system according to claim 12, wherein said signal processing device is further configured to dynamically modify said sound signal amplitude level for at least one first component of said far field sound detected by said first microphone system.

15. The noise error amplitude reduction system according to claim 12, wherein at least one of said gain values is determined based on a comparison of a relative sound signal amplitude level for said first far field sound component and said second far field sound component.

16. The noise error amplitude reduction system according to claim 12 , wherein said signal processing device is further configured to select at least one of said plurality of gain values based on a ratio of sound signal amplitude levels for said first far field sound component and said second far field component.

17. The noise error amplitude reduction system according to claim 16, wherein said signal processing device is further configured to set at least one of said plurality of gain values to zero if said sound signal amplitude levels for said first far field sound component and said second far field sound component are approximately equal.

18. The noise error amplitude reduction system according to claim 12, wherein said first microphone system and said second microphone system are configured so that near field sound originating in a near field environment relative to said first and second microphone systems produces a second difference in said sound signal amplitude at said first and second microphone systems, said second difference different than said first difference.

19. The noise error amplitude reduction system according to claim 12, wherein said far field environment comprises locations at least three feet distant from said first and second microphone systems.

20. The noise error amplitude reduction system according to claim 12, wherein said first and second microphone systems are configured by selecting at least one parameter of a first microphone associated with said first microphone system and a second microphone associated with said second microphone system.

21. The noise error amplitude reduction system according to claim 20, wherein said parameter is selected from the group consisting of a distance between said first and second microphone, a microphone field pattern, a microphone orientation, and acoustic feed system.

* * * * *